United States Patent
Beyer et al.

(12) 
(10) Patent No.: US 11,340,192 B1
(45) Date of Patent: May 24, 2022

(54) ION MOBILITY SPECTROMETER AND METHOD FOR OPERATING AN ION MOBILITY SPECTROMETER

(71) Applicant: Bruker Optik GmbH, Ettlingen (DE)

(72) Inventors: Achim Beyer, Brandis (DE); Uwe Renner, Leipzig (DE); Wolfgang Heller, Leipzig (DE); Sascha Faust, Leipzig (DE)

(73) Assignee: BRUKER OPTICS GMBH & CO. KG, Ettlingen (DE)

( * ) Notice: Subject to any disclaimer, the term of this patent is extended or adjusted under 35 U.S.C. 154(b) by 0 days.

(21) Appl. No.: 17/503,954

(22) Filed: Oct. 18, 2021

(30) Foreign Application Priority Data

Dec. 9, 2020 (DE) .......................... 102020132851.6

(51) Int. Cl.
*G01N 27/622* (2021.01)
*G01N 33/00* (2006.01)

(52) U.S. Cl.
CPC ....... *G01N 27/622* (2013.01); *G01N 33/0037* (2013.01)

(58) Field of Classification Search
CPC .......................... G01N 27/622; G01N 33/0037
See application file for complete search history.

(56) References Cited

U.S. PATENT DOCUMENTS

| | | |
|---|---|---|
| 7,973,279 B2 | 7/2011 | Baumbach et al. |
| 9,953,818 B2 | 4/2018 | Black et al. |
| 10,236,169 B2 | 3/2019 | Aliman et al. |
| 2009/0278038 A1 | 11/2009 | Baumbach et al. |
| 2011/0133746 A1 | 6/2011 | Shinada et al. |
| 2011/0253889 A1 | 10/2011 | Ishimaru et al. |
| 2013/0161507 A1 | 6/2013 | Nishimura et al. |
| 2017/0278690 A1 | 9/2017 | Aliman et al. |

FOREIGN PATENT DOCUMENTS

| | | |
|---|---|---|
| DE | 10 2006 050136 A1 | 5/2008 |
| DE | 10 2014 226039 A1 | 6/2016 |
| EP | 1963835 | 9/2008 |
| GB | 2584334 A | 12/2020 |

OTHER PUBLICATIONS

Translation of German Office Action dated Jul. 21, 2021 in connection with German Application No. 10 2020 132 851.6.
Goy et al., entitled: "A Gapless Micro-Dielectric-Barrier-Discharge Ion Source for Analytical Applications", ArXiv e-prints, 2016, pp. 1-34, accessible at http://arxiv.org/abs/1602.06242.
Jing Hu et al., "Dielectric Barrier Discharge in Analytical Spectrometry", Applied Spectroscopy Reviews, vol. 46, No. 5, pp. 368-387, Jul. 2011.

*Primary Examiner* — Jennifer Wecker
(74) *Attorney, Agent, or Firm* — Norris McLaughlin, P.A.

(57) ABSTRACT

Ion mobility spectrometers and methods for determining the ion mobility of a sample gas in dry air as drift gas are disclosed. The ion mobility spectrometers comprise a drift chamber, a reaction chamber, a dielectric barrier discharge ionisation source, a control unit, and a DBDI source, a pressure sensor, and a temperature sensor arranged in the chamber. A light source irradiates the DBDI source with light in a wavelength range from about 240 nm to about 480 nm. The control unit is designed to set an ignition voltage of the DBDI source and to control the light source depending on a determined pressure value and a determined temperature value. The methods control and utilize the control unit for operating the ion mobility spectrometer.

15 Claims, 5 Drawing Sheets

ION MOBILITY SPECTROMETER AND METHOD FOR OPERATING AN ION MOBILITY SPECTROMETER

This application claims foreign priority benefit under 35 U.S.C. § 119 of German Application No. 10 2020 132 851.6, filed Dec. 9, 2020.

FIELD OF THE DISCLOSURE

The present invention relates to an ion mobility spectrometer, in particular a mobile ion mobility spectrometer with improved plasma ignition, as well as a method for operating an ion mobility spectrometer, in particular with minimal ignition voltage.

TECHNICAL BACKGROUND

An ion mobility spectrometer is an instrument for characterising ions on the basis of their mobility in a drift medium under the action of an electromagnetic force. An ion mobility spectrometer usually has a reaction chamber and an adjacent drift chamber. The reaction chamber serves here to form reactant ions and to ionise the sample material. The drift chamber serves to determine the flight time or drift time of the ions formed.

The sample enters the reaction chamber via inlets and by means of a carrier gas and is ionised there by energy supply. The formed ions are guided by electric field action into the drift chamber, which is bounded, for example, on the inlet side by a grid as ion modulator and on the opposite side by a detector unit for ion flow measurement. In the drift chamber, the ions are moved towards the detector by further field action. A drift medium with defined physical-chemical properties contained in the drift chamber interacts with the ions and counteracts the movement of the ions mediated by the field effect. The transport of the ions in the drift chamber thus depends on the electric field strength as well as the interaction with the drift gas and can be characterised by the resulting drift velocity.

The ion mobility K is thus a measure of the molecular friction of an ion in a given drift medium under the effect of an electromagnetic force and is all the greater, the smaller this friction is. The ion mobility K is determined as a proportionality factor between the drift velocity v and the electric field component E that is effective in the direction of drift. In a first approximation, these variables have the following linear relationship $$v = K*E. \quad (1)$$

Provided that the properties of the drift medium in the drift chamber are homogeneous and the electric field in the drift region of the ions is constant, the ion mobility over a given path L is determined by determining the drift time t and the voltage difference U between the end and the start of the drift path on the basis of the following equation derived from (1):

$$K = L^2/(U*t). \quad (2)$$

The ion mobility K determined in this way always relates to a set drift medium and is not a specific constant of a particular ion. Rather, the value of the ion mobility is dependent on the interaction of the ion with the drift medium. If this interaction is assumed to be a collision process, its strength depends, according to the kinetic gas theory, on the mass of the collision partners involved, particle number density, pressure, and temperature of the drift medium and the cross-section of action of the ion with the molecules of the drift gas.

For ion mobility spectrometers used under atmospheric conditions, the range of values of the particle number density of the drift gas, which in turn depends on its temperature T and pressure p, extends over a wide range. For example, for the temperature T a range from −30° C. to +60° C. and for the pressure a range from 50 kPa to 110 kPa is possible. The dependence of the ion mobility on the particle number density is therefore eliminated by conversion to a normalised ion mobility. Even the normalised ion mobility $K_0(T)$, however, is temperature-dependent due to the dependence on the temperature-dependent cross-section of action of the particular interaction.

To determine the temperature-dependent normalised ion mobility $K_0(T)$, the measurements of a number of values, such as pressure, temperature, drift voltage, drift time, are necessary, and the relative measurement errors of the individual measurements may add up. It is therefore advantageous to use a reference-based method for determining the ion mobility instead. In this case, a reference substance is used, for which a normalised, temperature-dependent ion mobility $K_0^R(T)$ is known. If the physical-chemical conditions in the drift chamber are the same for the reference and sample measurements, the ion mobility of the sample substance $K_0^P(T)$ with the drift time $t_P$ can be calculated from the drift ratio $t_R/t_P$ by comparing the drift times of the reference substance and the sample substance by $K_0^P(T) = t_R/t_P * K_0^R(T)$. Advantageously, only the measurement error of the drift time measurement (which is in the range of the noise if the measurement sampling is sufficiently high) and the measurement error of the drift chamber temperature T (which only becomes significant if the ion mobility is strongly dependent on T) are relevant in this method. The reference substance is usually supplied externally, either via the sample supply line or via an additional gas inlet, which can be switched on via a valve. The reference substance, for example NOx, however, may also be produced in the ion mobility spectrometer.

When determining the ion mobility, it is therefore usually assumed that the drift medium has homogeneous and has constant physical-chemical properties. However, if air is used as the drift medium, for example, the proportion of water present in it can already significantly influence the value of the ion mobility. Therefore, dry air, preferably with an absolute water concentration of less than 100 ppm, should be used as a drift medium. Filter systems are usually used for this purpose.

In order for the drift medium to maintain its defined physical-chemical properties, it is also continuously renewed in the drift chamber by a gas flow. In other words, a continuous drift gas flow flows through the drift chamber, and the gas flow is determined by integrating the gas flow density over the cross-sectional area through which the gas flows. The gas flow density in this case is the product of gas concentration and gas velocity. The gas flow in the drift chamber is to superimposed on the ion flow and can in principle influence the effective drift time. However, the drift gas velocity of, for example, 4 cm/s is significantly smaller compared to the drift velocity of the ions of, for example, 4 m/s and is therefore often negligible for determining the ion mobility.

The ionisation of the sample to be analysed is first performed in an ion mobility spectrometer by supplying energy by means of an ionisation source. A large number of ionisation sources are known to a person skilled in the art, for example plasma sources. From the primary ions formed by means of the source, further product ions can be formed by complex molecular ion reactions and charge transfer processes with the sample substance. Due to the multi-stage character of ionisation, this takes place in the reaction chamber formed by the region between the ionisation source and the ion flow modulator.

The use of a DBDI source to ionize a sample gas for subsequent analysis by means of mass spectrometry is disclosed, for example, in US2013/0161507A1. Therein and also in US2011/0133746A1, the DBDI source is irradiated with blue or UV light. US 2013/0161507 A1 further mentions the dependence of the ignition voltage on the pressure and further prior art can be found in DE 10 2014 226 039 A1. The use of a DBDI source in an ion mobility spectrometer is also described in the US 2011/0253889 A1 and in DE 10 2006 050 136 A1

Efficient ionisation at the ionisation source is a prerequisite for subsequent ionisations as well as for efficient measurement operation. Although the amount of primary ions produced generally increases with higher energies, intensities or ionisation source powers, the amount of NOx compounds and formed ozone is also disadvantageous. In this context, ozone, nitrogen oxides and nitrogen oxide compounds (NOx compounds) are disadvantageous for use in the ion mobility spectrometer because they inhibit or prevent the ionisation of certain sample molecules. For example, Nox compounds bind negative charges due to their high electron affinity, which are therefore not available for further ionisation of the primary ions. The increased formation of ozone leads to unwanted side reactions and higher wear of components located in the gas circuit, such as pumps and sensors. This thus limits the energy, intensity or power range that can be used for sample ionisation.

The object of the present invention is to overcome or minimise the disadvantages of the prior art and to provide an improved ion mobility spectrometer and an improved method for operating an ion mobility spectrometer.

DETAILED DESCRIPTION OF THE DISCLOSURE

A first aspect of the present disclosure relates to an ion mobility spectrometer (IMS) for determining ion mobility of a sample, preferably an ion mobility spectrum of the sample, preferably from a drift time spectrum according to equation (2), in particular a sample present in a sample gas (sample and a carrier gas). The ion mobility of the sample is preferably determined in dry air as drift gas, in particular in air with a water concentration of less than 100 ppm. The ion mobility spectrometer has a drift chamber, in particular for determining the ion mobility of the ionised sample in a drift gas flow. The ion mobility spectrometer also has a reaction chamber, in particular for ionising the sample gas. A detailed design of the ion mobility spectrometer is explained in detail below.

The ion mobility spectrometer according to the invention has a dielectric barrier discharge ionisation source (referred to hereinafter as DBDI source) arranged in the reaction chamber for ionising the sample gas. The use of DBDI sources for the generation of low-temperature plasma in an ion mobility spectrometer is known in principle from the prior art. In a DBDI source of this kind, all electrodes are advantageously protected by a plasma-resistant dielectric and the average temperature of the produced low-temperature plasma corresponds approximately to the ambient temperature. The produced plasma on average has a neutral charge and consists of a mixture of negative charge carriers such as electrons and ions, positively charged ions and neutral particles.

The electrodes of the DBDI source are at least partially separated from the plasma by the dielectric, whereby they are protected against corrosion. No charge transfer takes place through this insulation, and therefore a plasma is generated by means of alternating voltage, in particular high-frequency alternating voltage. The plasma is ignited under atmospheric conditions in a zone of a few millimetres between the electrodes.

Starting from the molecules that are significantly present in air, such as molecular oxygen and nitrogen, the composition of the plasma is determined by complex chemical reactions of the ions and neutral gas particles, with ozone and oxygen compounds of nitrogen also being produced as by-products. The ions formed locally are removed from the source by an electric field superimposed on the discharge field.

A prerequisite for the formation of such a plasma at the DBDI source is high reduced electric field strengths, which are achieved by applying a high voltage to the electrodes. According to Paschen's law, a minimum ignition voltage is necessary for the plasma to form, which can be different for direct and alternating voltage. After ignition of the plasma, it can be maintained with a lower voltage.

The ion mobility spectrometer also has a pressure sensor arranged in the reaction chamber and a temperature sensor arranged in the reaction chamber, and also a control unit connected to the pressure sensor, the temperature sensor and the DBDI source. The control unit is designed in accordance with the invention to set an ignition voltage of the DBDI source depending on a pressure value determined by the pressure sensor and a temperature value determined by the temperature sensor. The ignition process of the plasma at the DBDI source is pressure- and temperature-dependent on account of the dependency on the reduced electric field strength. Since complex kinetic processes take place during plasma formation, this is also explicitly dependent on the temperature. The pressure sensor and the temperature sensor are preferably arranged in the vicinity of the DBDI source, for example at a distance of less than 5 cm, particularly preferably of less than 2 cm. The sensors are likewise preferably arranged in a gas outlet of the reaction chamber.

In the ion mobility spectrometer according to the invention, the plasma is thus ignited and maintained depending on temperature and pressure of the gas flowing past, controlled by means of the correspondingly configured control unit. The control unit preferably sets the optimum field strength and high-voltage parameters for amplitude and frequency of the ignition voltage and updates these in the event that the gas state changes. The control unit likewise preferably sets the ignition voltage depending on the electrode assembly of the particular type of DBDI source used. A continuous (constant) measurement of the gas temperature and of the gas pressure is particularly preferably performed in the vicinity of the DBDI source by the pressure and temperature sensors, in order to ensure, in a sustained manner, the ignition and maintenance of the plasma with minimal ignition voltage.

In a first approach, with a predefined ignition frequency or an ignition frequency determined on the basis of the DBDI source type (in particular the electrode assembly) and with a constant gas flow, the optimal ignition voltage is dependent exclusively on pressure and temperature, since these parameters determine the gas density and thus the reduced field strength. Tests performed by the inventors have shown that a setting of the ignition voltage on the basis of pressure and temperature is sufficient to ensure operation with minimal ignition voltage.

The ion mobility spectrometer according to the invention also has a light source for irradiating the DBDI source with light in a wavelength range from 240 nm to 480 nm, preferably with light in a wavelength range from 280 nm to 480 nm. The light source is consequently arranged within or close to the reaction chamber and is positioned relative to the DBDI source or is connected thereto via a light guide such that the DBDI source is illuminated with the light emitted by the light source. The control unit of the ion mobility spectrometer is also connected to the light source and is designed to control the light source. In particular, the control unit of the ion mobility spectrometer is designed to activate and to deactivate the light source. The light source is preferably designed to set the intensity in a variable manner.

As already described, the ignition of the plasma in the switch-on phase is a critical process. As found by the inventors, the ignition of the plasma in dry, clean air (in particular with a water concentration of less than 100 ppm) may be significantly temporally delayed following a relatively long period of inoperation. This is unacceptable in particular for a mobile device with the requirement of rapid operational readiness. In principle, in such a case the ignition voltage could be significantly increased, whereby, however, extremely disruptive NOx compounds would be formed. In addition, the dielectric of the DBDI source would be subjected to a significantly high (over)load, with the threat of premature failure or a high probability of flashover in the electrode region due to the initially very large plasma zone when ignition is initiated with increased voltage. It is known in principle that light can be used to reduce the ignition voltage of a plasma. However, tests performed by the inventors have shown that, for example, green or red light with a low radiant power of less than 1 W does not improve the ignition behaviour at all. It was further found by way of experimentation that, for dry air, the time for ignition can be significantly reduced by blue to ultraviolet light, in particular in the wavelength range 240 nm to 480 nm, particularly preferably in the wavelength range 280 nm to 480 nm. This wavelength range corresponds to the second positive series of molecular nitrogen. In principle, wavelengths shorter than 240 nm can also be used to reduce the ignition voltage, but this significantly increases the formation rate of ozone and of NOx compounds.

The control of the light source by the control unit of the ion mobility spectrometer according to the invention thus advantageously enables an additional reduction of the necessary ignition voltage as required, in particular when starting up again. This is also particularly advantageous with regard to the shorter service life of typical light sources (typically less than 1000 hours) compared to the average service life of an ion mobility spectrometer (up to 10,000 hours without maintenance). The light source is preferably a light-emitting diode or laser diode with a corresponding wavelength.

In a preferred embodiment of the ion mobility spectrometer according to the invention, this further comprises an ion detector arranged in the drift chamber. According to this embodiment, the control unit is further designed to receive a signal value from the ion detector. The ion detector is preferably designed, possibly in combination with a switching grid explained below, to detect ions arriving at a detector unit. The arriving ions can be identified here by the drift time in the drift chamber, in particular from the switching grid to the ion detector, and possibly on the basis of the charge transported by the ions. A signal value according to this embodiment therefore preferably corresponds to an ion species, for example to product ions or NOx ions, as well as to a quantity of these ion species. On the basis of the signal value obtained from the ion detector, the control unit can thus determine in particular the type and/or the quantity of ions formed in the reaction chamber. According to this embodiment, the control unit is further designed to control the DBDI source and/or the light source on the basis of the signal value obtained from the ion detector. This preferably enables a control of the DBDI source and/or the light source in respect of the targeted generation and/or targeted avoidance of certain ion species.

Particularly preferably, the control unit of the ion mobility spectrometer according to the invention is designed in accordance with this embodiment to control the light source in such a way that a first signal value of the ion detector exceeds a first limit value. In a preferred embodiment, the first signal value is an integral value or sum value calculated over a larger drift time range, in particular the entire drift time range to be detected, and is determined from a drift time spectrum recorded with the grating open and represents a measure of the charge generated by the DBDI source. Alternatively, the ion detector first evaluates a first signal value of which the position in the ion mobility spectrum preferably corresponds to a certain ion species. This ion species is preferably predetermined and particularly preferably corresponds to a product ion to be detected or expected. Alternatively, however, it may also be any other ion species. Further preferably, the first signal value corresponds to a non-specific integral of the spectrum or to a non-modulated total ion flow in order to detect the ignition of a plasma.

According to this embodiment, the first signal value is preferably proportional to the amount of ions of the particular species generated in the reaction chamber. This is particularly true for small amplitudes in the drift spectrum. Preferably, according to this embodiment, the control unit is designed to determine if the first signal value falls below a predetermined limit value.

This may indicate that ignition of the plasma has not been successful or that the plasma cannot be maintained at a constant level. The control unit of this embodiment is further preferably designed, in response to determining that the first signal value falls below the predetermined limit value, to control the light source to irradiate the DBDI source with light having a wavelength of 240 nm to 480 nm, preferably 280 nm to 480 nm. Thus, the ignition of the plasma or its maintenance can be supported by the control unit. Also preferably, the control unit receives a plurality of signal values, for example for different ion species, and performs a comparison of these signal values with one or more limit values to determine whether illumination of the DBDI source is indicated or necessary, and lastly controls the light source based on the result of these comparisons.

In a likewise particularly preferred embodiment of the ion mobility spectrometer according to the invention, the control unit is further designed to set an ignition voltage of the DBDI source in such a way that, for the determined pressure and temperature values, a first signal value of an ion detector exceeds a first limit value and a second signal value of the ion detector falls below a second limit value. Particularly preferably, according to this embodiment, the control unit receives a first signal value corresponding to a first ion species and a second signal value corresponding to a second ion species. The control unit can then determine whether the first signal value exceeds a first limit value and whether the second signal value falls below a second limit value and can control the DBDI source on the basis of these comparisons.

Particularly preferably, the control unit according to this embodiment is designed to determine the first signal value on the basis of a peak of a product ion and the second signal value on the basis of a peak of a NOx ion in an ion mobility spectrum determined with the ion detector. In other words, the control unit in this case receives an ion mobility spectrum determined by the ion detector or creates such a spectrum on the basis of data received from the ion detector. Further preferably, the control unit identifies a peak of a product ion and a peak of a NOx ion in the ion mobility spectrum on the basis of predefined information (for example, on the basis of a user input and/or a memory value) and reads the signal values corresponding to the particular peak positions from the ion mobility spectrum. Consequently, exceeding a first limit value by the first signal value corresponds to the presence of more than a certain amount of product ions in the drift chamber, and falling below a second limit value by the second signal value corresponds to the presence of less than a certain amount of NOx ions in the drift chamber.

The aforementioned preferred embodiments enable advantageous operation of the ion mobility spectrometer with a minimum ignition voltage that ensures sufficient production of product ions and minimal contamination by NOx ions. As explained above, an optimum ignition voltage exists when a minimum level of product ions (primary ions, sample ions) can be reliably maintained and the production of NOx ions is minimised. This optimum ignition voltage is preferably determined on the basis of an ion mobility spectrum, in particular taking into account the particular peak positions. It is particularly preferred to avoid the formation of all NOx ions, i.e. to minimise the individual intensities or integrals (sums) of the intensities in an interval around the NOx peak positions to zero. Also preferred is the formation of a sufficient amount of product ions (primary ions, sample ions), i.e. ensuring individual intensities or integrals (sums) of intensities in an interval around the particular peak positions above a limit value.

The determination of the optimum ignition voltage is thus a multi-dimensional optimisation problem, which is preferably carried out computationally taking into account predetermined (first and second) limit values. Particularly preferably, the optimisation problem is solved by the control unit according to the invention using data received from the ion detector. Also preferably, this optimisation problem is solved on the basis of data determined in a test stand. Particularly preferably, this optimisation problem is solved using mathematical algorithms, such as the method of least squares or by means of artificial intelligence and parameter variation. Particularly preferably, the optimisation problem is solved for a specific DBDI source by determining the minimum ignition voltage under defined thermodynamic conditions in a test stand, for example a climatic chamber, by varying the pressure and temperature and, if necessary, the frequency, while dry, clean air with a water concentration of less than 100 ppm at a defined gas flow flows around the DBDI source.

As a result of the optimisation, a pressure-temperature matrix table is obtained in accordance with the invention for a certain ignition frequency and contains the desired minimum ignition voltage as a result. By interpolation of the data, a functional relationship can be presented. The obtained data (table) or relationships are preferably stored in a conventional manner in non-volatile memories or are stored as programs in algorithms. Further preferably, the ion mobility spectrometer according to the invention has the obtained data in the form of a lookup table stored in an internal memory. The control unit is then further designed to read out the optimum ignition voltage and optionally the ignition frequency from the lookup table stored in the memory on the basis of the pressure and temperature values recorded by means of the sensors and to control the DBDI source with this ignition voltage and optionally ignition frequency.

In a particularly preferred embodiment of the ion mobility spectrometer according to the invention, the light source is designed to irradiate the DBDI source with light having a wavelength of 405 nm and/or an optical power of less than 100 mW. The inventors have found by way of experimentation that wavelengths of 405 nm are particularly suitable for lowering the ignition voltage at a DBDI source for igniting a low-temperature plasma in dried air. Such light sources are also used, for example, as laser diodes in Blu-ray players or as UV LEDs for curing resins in 3D printers and are therefore advantageously available in a variety of commercial forms. In a likewise preferred embodiment, the light source for irradiating the DBDI source with light is a UV LED or blue LED with a wavelength of 365 nm, 385 nm, 395 nm, or 450 nm, such as those used for curing adhesives. Particularly advantageous when using such sources with a narrow spectral range for ignition is that only a low total optical radiation power of less than 100 mW is required, especially compared to more broadband sources, such as quartz lamps. In addition, the above-mentioned laser diodes or UV LEDs are manufactured in semiconductor technology and therefore advantageously have a lower electrical power loss, which means lower energy consumption and thus a longer operating time for mobile devices.

In the ion mobility spectrometer according to the invention the drift chamber is preferably cylindrical and also preferably is designed for transporting ions from a switching grid, preferably consisting of at least one grid electrode, to an ion detector. The drift chamber here is further designed in such a way that the ion flow therein is against an axial drift gas flow. The drift gas flow thus runs from the direction of the ion detector in the direction of the switching grid. A drift velocity is dependent here both on the effect of an electric field between the switching grid and the ion detector and on the interaction of the ions with the drift gas flow. Preferably, for a given electric field and a given drift gas flow, a constant drift velocity establishes itself for a given ion type, so that no macroscopic acceleration of the ions in the drift chamber occurs. In the context of the present disclosure, the axial direction refers to the height of the cylindrical drift chamber.

In the ion mobility spectrometer according to the invention, the reaction chamber is preferably also cylindrical and adjacent to the drift chamber in the axial direction. The axial direction refers here to the height of the cylindrical reaction chamber and is preferably identical to the axial direction of the cylindrical drift chamber. The reaction chamber preferably has a sample gas inlet adjacent to the switching grid for introducing the sample gas. The sample gas inlet is designed here in such a way that the sample gas mixes with the drift gas. The sample gas inlet is located here on a side facing away from the drift chamber, adjacently to the switching grid. At the opposite end of the reaction chamber there is a gas outlet for discharging drift gas and sample gas, i.e., the mixture of these two gases. Furthermore, the DBDI source is arranged at the gas outlet of the ion mobility spectrometer according to the invention. Also preferably, the pressure sensor and the temperature sensor are arranged at or in the gas outlet.

The DBDI source of the ion mobility spectrometer according to the invention can be realised by a gas-tight glass body filled with the noble gases helium, krypton or argon, to which a high-frequency high-voltage field is applied to generate vacuum UV radiation. The vacuum UV radiation exits the glass body through a thin window that is transparent to the spectral range and causes photoionisation of the sample gas, with the electrodes being insulated by the glass and located outside the plasma.

Electrodes that are fully protected by a plasma-resistant insulator, such as corona-resistant polyimide or a glass coating, are likewise preferably used for the DBDI source. Particularly preferably used are wire electrodes of which the wires are formed of, for example, tungsten and are insulated with thin glass. Such a wire electrode is described in Coy et al. 2016. A Gapless Micro-Dielectric-Barrier-Discharge Ion Source for Analytical Applications. ArXiv e-prints, 2016. 1602. http://arxiv.org/abs/1602.06242, the content of which is hereby fully referenced. When high-frequency high-voltage is applied to such an electrode, plasma forms in the surrounding air at the contact points of the glass casing. Coy et al. already observed the formation of NOx compounds in this process. A net-like arrangement of such electrodes, in which wires touch each other in pairs similarly to single contact, is also particularly preferred for use in the ion mobility spectrometer according to the invention.

Particularly preferably, the ion mobility spectrometer according to the invention has a modular DBDI source, which is easier to integrate into existing cylindrical setups of ion mobility spectrometers than a DBDI source fully integrated into the base tube. The DBDI source is preferably realised as a layered arrangement with alternating insulator and electrode layers, wherein the electrodes are embedded in an insulator matrix, and wherein the layered arrangement is perforated to ensure the flow and transport of the sample gas.

In a preferred embodiment of the ion mobility spectrometer according to the invention, the reaction chamber is cylindrical and the DBDI source has an insulating perforated disc of which the outer circumference is integrated into an edge of the reaction chamber. For example, the reaction chamber is constructed from a plurality of annular segments and the DBDI source is integrated as a module between two such annular segments. However, in addition, the perforated disc may also be integrated into a segment of the reaction chamber or otherwise into an outer circumference of the reaction chamber. At least two oppositely poled electrodes extend from the outer circumference of the insulating perforated disc towards an inner circumference of the insulating perforated disc. Consequently, the electrodes extend at least proportionally in a radial direction, and the electrodes preferably also extend beyond the outer circumference and/or the inner circumference. At least one plasma zone is formed between the at least two oppositely poled electrodes.

The outer circumference of the perforated disc is preferably larger than an inner circumference of the reaction chamber and the inner circumference of the perforated disc is preferably equal to or smaller than the inner circumference of the reaction chamber. In an embodiment with an inner circumference of the perforated disc that is smaller than the inner circumference of the reaction chamber, the electrodes are preferably arranged in a middle insulator layer so as not to come into contact with air. Further preferably, the electrodes are exposed along or near the inner circumference, wherein oppositely poled electrodes are separated from each other by a middle insulating layer so that a plasma zone is built up between them. The narrowed smaller inner circumference of the perforated disc advantageously causes rapid removal of the ozone and nitrogen oxides forming in the plasma zone. In the case of high-frequency ignition voltage, care must be taken to ensure a small electrode area because of the capacitor arrangement formed; the electrodes are preferably formed as thin rings or narrow parallel sectors and are preferably led to the outside via thin, diverging connecting wires.

In a particularly preferred embodiment of the ion mobility spectrometer according to the invention, the DBDI source with insulating perforated disc has at least two insulating spokes each extending over a central opening of the insulating perforated disc. The insulating spokes cross each other within the central aperture and each support at least one of the paired electrodes of opposite polarity. For example, one electrode is arranged per spoke. Alternatively, one electrode is arranged on each of the two surfaces of the spoke pointing in different directions in the axial direction.

Such a DBDI source can be advantageously integrated into a conventional cylindrical edge structure of an ion mobility spectrometer as a voltage-insulating segment and also has a stabilising skeletal structure in the form of spokes or ribs that cross in the centre of the cylinder of the reaction chamber and serve as supports for the electrodes of the DBDI source. Particularly preferably, the DBDI source has a cylindrical skeletonised insulating edge segment (perforated disc) with spokes or ribs made of the same insulating material. The DBDI source is preferably manufactured in a manufacturing process, particularly preferably by milling or other machining processes, or in an additive process, particularly preferably by 3D printing. Preferably, the insulating perforated disc and the insulating spokes are monolithic and/or are formed from an electrically insulating glass, plastic, quartz, or ceramic.

The use of spokes as carriers for the electrodes and their crossing on the axis of symmetry of the reaction chamber enables a central formation of a plasma zone around which the sample gas flow (possibly mixed with drift gas flow) flows advantageously. Therefore, neutral ozone and nitrogen oxide molecules are safely transported away to the gas outlet and primary ions formed in the plasma zone can effectively react with the neutral sample gas flow and produce a maximum yield of product ions.

A DBDI source according to this embodiment has at least two insulating spokes. However, there can also be more than two spokes, each of which accommodates an electrode and/or acts as a stabilising support. Particularly preferably, the spokes taper in the radial direction of the DBDI source and thus enable a high mechanical stability as well as a small mutual air gap (discharge distance) of the plasma zone on the axis of symmetry of the reaction chamber. A taper in the axial direction of the reaction chamber is also preferred in the direction of the gas outlet, but not necessary. The spokes do not necessarily run from edge to edge of the DBDI source. It is also preferred that two spokes meet in a V-shape in the centre of the DBDI source.

In a likewise preferred embodiment of the ion mobility spectrometer according to the invention, the reaction chamber and the perforated disc are concentric and have a circular-cylindrical shape. According to this embodiment, the at least two insulating spokes are radially oriented and cross on an axis of symmetry of the reaction chamber and the perforated disc. At least one plasma zone is thus formed at the crossing point of the at least two insulating spokes and thus on the common axis of symmetry of the rotational symmetry of the reaction chamber and the perforated disc. In this embodiment, the drift chamber and the reaction chamber particularly preferably have a circular-cylindrical shape. In other words, the drift chamber and the reaction chamber have a circular cross-sectional area, with a radial direction of these circular areas being perpendicular to the axial direction of the particular chamber. Also preferably, the perforated disc has a circular cross-sectional area. Particularly preferably, the cross-sectional areas of the drift chamber, reaction chamber and perforated disc are concentric with each other, the axial directions thus coinciding. Also preferably, the gas outlet of the reaction chamber is arranged concentrically with the reaction chamber and the drift chamber with respect to the axial direction.

Also preferred is an embodiment of the DBDI source with a plurality of intersecting spokes and with a plurality of plasma zones formed. Particularly preferably, the DBDI source of this embodiment has a plurality of intersecting spokes in a star-shaped arrangement, the crossing point thus lying on the axis of symmetry. Preferably, at least N plasma zones can be generated with a plurality of non-continuous spokes in a preferably symmetrical arrangement with an even number 2N and preferably equal sector angles between the spokes in the air sectors.

In a likewise preferred embodiment, the reaction chamber of the ion mobility spectrometer has a gas outlet and the DBDI source is arranged at the gas outlet. According to this embodiment, the electrodes are preferably arranged only on one side of the DBDI source facing the gas outlet. This has the advantage, particularly in the case of a unidirectional flow around the DBDI source, that neutral NOx compounds formed by ozone and radicals reach the gas outlet directly and are not further ionised. This thus ensures an optimal flow around the DBDI source. Also preferably, the pressure sensor and the temperature sensor are arranged at or in the gas outlet.

Further preferably, each of the insulating spokes of the DBDI source has a trench and one of the electrodes of the DBDI source is located in such a trench. It is therefore preferable to produce grooves or trenches in the insulating support structure of the spokes to accommodate the electrodes. These are located on both sides or on one side of the spokes, preferably on the gas outlet side. Depending on the size of the DBDI source, various technologies can be used to form the trenches, such as grinding, milling, engraving, etching, but also precise machining methods of microstructuring or semiconductor technology. In a trench, the electrode is preferably fastened to the bottom of the trench, for example by pressing or gluing. Also preferably, the electrode is deposited as a conductive coating in the trench, for example by electroplating or by a method of thin-film technology. Preferred electrode materials are metals, metallic alloys and thin semi-conducting materials, for example indium tin oxide (ITO). The trench depth is also preferably selected in such a way that a discharge along the shortest air path between the electrodes only takes place in a region intended for the plasma zone. Thus, a discharge over the edge of the trench can be advantageously avoided, even without an insulating electrode coating.

However, it is further preferred that the electrodes are coated with an insulating sealant, preferably with resin, adhesive or silicates. Therefore, a trench depth can be advantageously selected to be smaller, and it is also advantageously possible to deposit the electrodes on planar spokes. The coating further advantageously protects the electrodes from aggressive gases such as ozone or nitrogen oxides in the environment of the plasma source as well as from the primary ions formed there and their secondary products. Particularly preferred is the complete sealing of the trenches, which advantageously also minimises deposits on the surface. Such sealing is achieved using suitable coating technologies. In a particularly preferred embodiment of the ion mobility spectrometer according to the invention, the insulating seal is made of a UV-transparent material and is designed as a light guide for the light from the light source. In particular, the insulating seal has an exit point for the light near the at least one plasma zone. This exit point is created, for example, by surface modification of the seal.

In a likewise preferred embodiment, the spokes are provided with holes in the radial direction, into which the electrodes are inserted. Particularly preferably, at least two continuously staggered holes are provided per spoke, separated by a thin layer of the insulating carrier of less than, for example, 1 mm. Likewise, only one hole is arranged per spoke, for example, in the case of non-continuous spokes, only one hole with an electrode inserted therein is provided and the plasma zone is formed between opposing end faces of two spokes.

Also preferably, a gas outlet of the reaction chamber has a smaller flow cross-section than the reaction chamber and/or the drift chamber. Particularly preferably, the flow cross-section of the reaction chamber is smaller than the flow cross-section of the drift chamber and the flow cross-section of the gas outlet is smaller than the flow cross-section of the reaction chamber. The increasing tapering of the flow cross-sections in this case advantageously causes an increase in the gas flows at the DBDI source.

Particularly preferably, the DBDI source in the ion mobility spectrometer according to the invention is placed in the gas outlet, and the gas outlet has a flow cross-section of 6 mm or less. The arrangement in the gas outlet in this case preferably also denotes an arrangement of the ionisation source in the reaction chamber near the gas outlet. The flow velocity of the gas flow increases according to the ratio of the flow cross-section of the reaction chamber to the flow cross-section in the gas outlet. Advantageously, in the ion mobility spectrometer according to the invention, undesired reaction products of the ionisation source are thus discharged directly through the gas outlet, and a backflow or diffusion into the reaction chamber is advantageously also prevented. Also particularly preferably, the pressure sensor and the temperature sensor are arranged at or in the gas outlet.

In a likewise preferred embodiment of the ion mobility spectrometer, this further comprises at least one potential source arranged in the reaction chamber for generating an electric field for transporting ions formed at the DBDI source away in the direction of the drift chamber. This potential source advantageously enables primary ions formed at the DBDI source to be transported away from the latter and thus prevents a recombination of the ions at the DBDI source. Also preferably, the mean electrical potential of the DBDI source is coupled to the potential of the surrounding reaction chamber in order to optimise the formation rate of the product ions. Particularly preferably, a field support ring located in the reaction chamber in the immediate vicinity of the DBDI source is used as potential source. By means of the potential source and the field of the DBDI source as reference potential, an axial field is created for the transport of the primary ions into the reaction chamber. In addition, by means of the potential source, which preferably serves as a field support ring, a radial field component in relation to the DBDI source can also be achieved in the reaction chamber and thus a widening of the primary ion beam, which is initially small in diameter. Preferably, the potential source, for example the nearest field support ring, is therefore at an increased potential compared to the mean potential of the DBDI source and surrounds the DBDI source centrically. Therefore, the neutral sample molecules flowing past the DBDI source at a greater radial distance are also advantageously ionised. Advantageously, this is followed by a zone with drift velocity reduction, which is created by a small or disappearing potential difference to the next neighbouring field support ring in the direction of the drift chamber. This thus increases the residence time of the primary ions and also the probability of the formation of product ions from the primary ions.

Further preferably, the ion mobility spectrometer according to the invention has a drift gas inlet arranged in the region of the ion detector. In a cylindrical drift chamber, the ion detector is preferably arranged on the top surface of the drift chamber facing away from the reaction chamber. At least one drift gas inlet is preferably arranged adjacently to the detector, for example concentrically around a circular detector. Preferably, the drift gas inlet is formed as a ring opening arranged concentrically around the detector, which advantageously allows a laminar formation of the drift flow.

Also preferably, the ion mobility spectrometer according to the invention has a drift gas supply for the controllable supply of drift gas and a sample gas supply for the controllable supply of sample gas. The supplies are preferably arranged outside the reaction chamber and the drift chamber, wherein the sample gas supply feeds sample gas to the sample gas inlet (carrier gas with or without sample material) via the sample gas supply line, and wherein the drift gas supply feeds the drift gas inlet with drift gas. For this purpose, each of the supplies can have one or more pumps and/or one or more valves and can have gas supply lines designed, for example, as hoses, piping or channels.

Another aspect of the present invention relates to a method of a control unit for operating an ion mobility spectrometer having a drift chamber and a reaction chamber. The method is used for determining an ion mobility of a sample gas in dry air as a drift gas and has the following method steps. In one method step, a pressure value detected by a pressure sensor arranged in the reaction chamber and a temperature value detected by a temperature sensor arranged in the reaction chamber are determined, and, in a further method step, an ignition voltage of a DBDI source arranged in the reaction chamber is set depending on the determined pressure value and the determined temperature value. Furthermore, in the method according to the invention, the light source arranged in the reaction chamber according to the invention is controlled to irradiate the DBDI source with light in a wavelength range from 240 nm to 480 nm, preferably with light in a wavelength range from 280 nm to 480 nm.

According to the invention, the ignition voltage of the DBDI source is advantageously set to a minimum value on the basis of the pressure and temperature measured in the reaction chamber. The optimum ignition voltage is also preferably determined here for the used DBDI source and/or for a fixed ignition voltage frequency. By setting the minimum and optimum ignition voltage, sufficient generation of sample ions is advantageously ensured and at the same time the formation of NOx ions is largely avoided.

The optimum ignition voltage is further ensured by irradiating the DBDI source with light in a wavelength range of 240 to 480 nm, preferably with light of a wavelength of 280 nm to 480 nm, wherein such irradiation of the DBDI source in dry air with a water content of less than 100 ppm both lowers the ignition voltage of the plasma and shortens the time for igniting the plasma. Advantageously, in the wavelength range mentioned, an optical radiation power of less than 100 mW is sufficient to significantly support plasma ignition. Particularly preferred is the irradiation of the DBDI source with wavelengths of 365 nm, 385 nm, 395 nm, 405 nm or 450 nm.

The irradiation is preferably performed for a short time until the onset of ionisation, which can be recognised in the drift time spectrum on the basis of the intensities, for example for the product ions. A minimum value of the intensity or the integral in a predefined interval can be used as a criterion for switching off the light source, and falling below the minimum value causes the light source to be switched on again. Pulsed continuous operation of the light source is also preferred. The pulse width is preferably adapted to the ambient conditions, such as humidity, pressure, and temperature at or close to the DBDI source.

In the method according to the invention, a signal value is preferably also received from an ion detector arranged in the drift chamber and the ignition voltage is set depending on the pressure and temperature values, so that a first signal value of the ion detector exceeds a first limit value, and a second signal value of the ion detector falls below a second limit value. Also preferably, the light source is controlled so that a first signal value of the ion detector exceeds a first limit value. The optimum ignition voltage is preferably determined on the basis of the signal values of the ion detector of the ion mobility spectrometer and by the control unit of the ion mobility spectrometer. The signal values are preferably evaluated empirically and, on the basis of the evaluation, the optimum ignition voltage is preferably stored in a lookup table for a specific combination of pressure and temperature.

As already explained above, suppression of ion formation from NOx compounds is possible by using the lowest possible high-voltage amplitude for ignition and maintenance of the plasma. At the same time, the minimum ignition voltage of the plasma depends on the gas density and thus, according to the ideal gas law, on the temperature and the absolute pressure of the gas, however, these values can change during operation. According to the invention, the ignition and maintenance of the plasma is controlled depending on the temperature and pressure of the gas flowing past by means of a control system which sets the optimum high-voltage parameters for amplitude and frequency and adjusts them in the event of a change. In order to ensure the ignition and maintenance of the plasma at minimum voltage, the gas temperature and gas pressure in the vicinity of the ionisation source are further preferably measured by corresponding sensors, and the drift time spectrum is measured by an ion detector.

The method steps of the method according to the invention can be implemented by electrical or electronic parts or components (hardware) by firmware (ASIC) or by executing a suitable program (software). Also preferably, the method according to the invention is realised or implemented by a combination of hardware, firmware and/or software. For example, individual components for carrying out individual method steps are designed as a separate integrated circuit or are arranged on a common integrated circuit. Individual components for carrying out individual method steps are also preferably arranged on a (flexible) printed circuit board (FPCB/PCB), a tape carrier package (TCP) or another substrate.

The individual method steps of the method according to the invention are further preferably designed as one or more processes which run on one or more processors in one or more electronic computing devices and are generated during the execution of one or more computer programs. The computing devices are preferably designed here to cooperate with other components, for example a memory, an interface and one or more sensors, in order to implement the functionalities described herein. The instructions of the computer programs are preferably stored here in a memory, such as a RAM element. However, the computer programs can also be stored in a non-volatile storage medium, such as a CD-ROM, a flash memory or the like.

It is further apparent to a person skilled in the art that the functionalities of several computers (data processing devices) can be combined or combined in a single device or that the functionality of a particular data processing device can be distributed to a plurality of devices in order to carry out the steps of the method according to the invention without deviating from the method described in accordance with the invention. The preferred embodiments of the method according to the invention correspond to preferred embodiments of the ion mobility spectrometer according to the invention.

DESCRIPTION OF THE FIGURES

Exemplary embodiments of the present invention are explained below with reference to the accompanying drawings. The drawings show.

Figure 1:
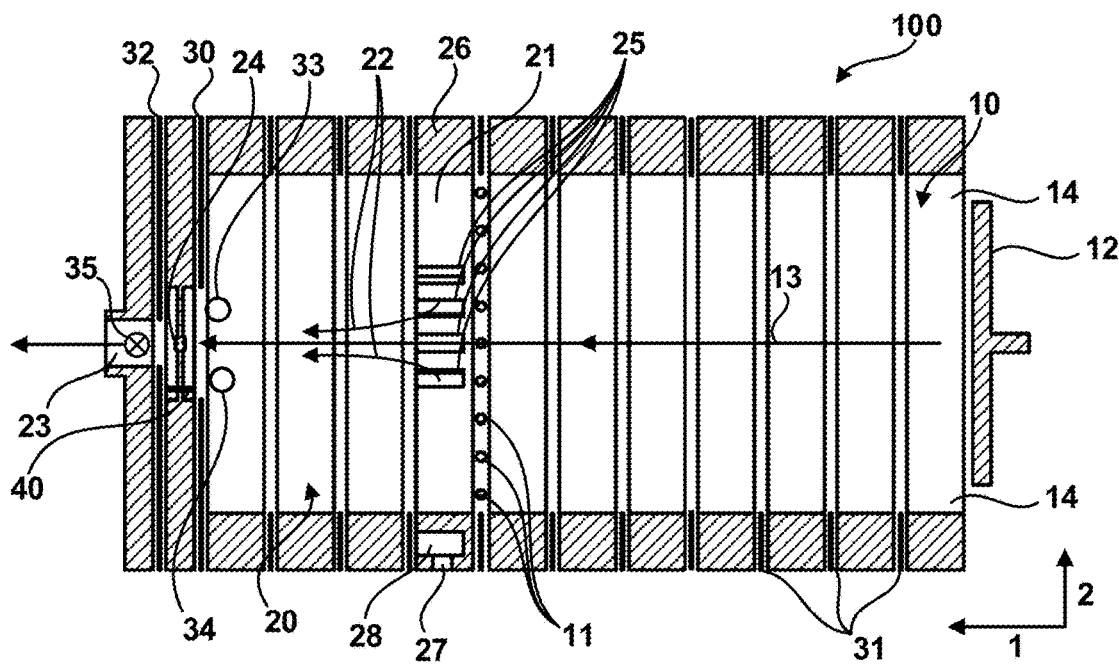
FIG. 1 is a schematic lateral sectional view of an ion mobility spectrometer according to an embodiment.

An ion mobility spectrometer 100 according to an embodiment of the present disclosure is shown in FIG. 1 in a schematic side view. The ion mobility spectrometer 100 has a cylindrical drift chamber 10 and a cylindrical reaction chamber 20 adjacent thereto in the axial direction 1. The drift chamber 10 is delimited on one side facing the reaction chamber 20 by a switching grid 11. On a side opposite the switching grid 11, the drift chamber 10 is delimited by an ion detector 12 and the reaction chamber 20 is delimited by a gas outlet 23.

A drift gas inlet 14 is arranged annularly around the ion detector 12. A sample gas inlet 21 is arranged in the reaction chamber 20 adjacent to the switching grid 11 and has gas inlets 25 arranged in pairs opposite each other on an inner circumference of the reaction chamber 20.

A dielectric barrier discharge ionisation source, DBDI source, 24 is further arranged in the reaction chamber 20 near the gas outlet 23.

During operation of the ion mobility spectrometer 100, a drift gas 13, in particular dry air with a water content of less than 100 ppm, is introduced into the drift chamber 10 by means of a drift gas supply (not shown) through the drift gas inlet 14 at a defined flow velocity, and in this case has, for example, a mean flow velocity of 4 cm/s. The drift gas 13 flows through the drift chamber 10, the switching grid 11 and the reaction chamber 20 and leaves the ion mobility spectrometer 100 through the gas outlet 23. Furthermore, during operation of the ion mobility spectrometer 100, a sample gas 22 consisting of sample material contained in a carrier gas can be introduced into the reaction chamber 20 through a sample gas inlet 21.

The sample gas 22 mixes with the drift gas stream 13 in an axial direction downstream of the sample gas inlet 21, and the total gas flow formed of the sample gas stream 22 and the drift gas stream 22 flows towards the gas outlet 23, wherein the total gas flow is increased due to the smaller flow cross-section of the gas outlet 23. Before the increased total gas flow leaves the ion mobility spectrometer 100 through the gas outlet 23, it flows around the DBDI source 24, reaching flow velocities of more than 50 cm/s depending on the flow rate of the drift gas 13. At the DBDI source 24, the sample material is ionised indirectly via the formed reactant ions by a dielectric barrier discharge or directly by the produced vacuum UV light. In addition, components of the air used as drift gas 13 may be ionised. In the vicinity of the DBDI source 24, an LED or laser diode is arranged as a light source 35, by means of which the DBDI source 24 can be directly illuminated. When switched on, the LED or laser diode 35 ensures ignition of the plasma under dry ambient conditions, in particular when both the drift gas and the carrier gas or sample gas are dry, for example with a water concentration of the total flow of less than 100 ppm. Also located near the DBDI source 24 are a pressure sensor 33 and a temperature sensor 34 in the reaction chamber 20. As an alternative to the illustration in FIG. 1, the pressure sensor 33 and the temperature sensor 34 can also be arranged, particularly preferably, in the gas outlet 23 of the reaction chamber 20.

The reaction chamber 20 also has a local potential source 30 by means of which an electrical voltage can be built up with respect to a reference source 32 (ground). Depending on the potential difference thus generated between DBDI source 24 and potential source 30, ions of a certain polarity are moved in the direction of the switching grid 11 and against the total gas flow. The movement is further mediated by further potential support rings (field support rings) 31, which are arranged both in the reaction chamber 20 and in the drift chamber 10. In this case, mainly ions with a ratio of ion velocity and flow velocity greater than one are moved against the total gas flow towards the switching grid 11, while others are guided by the high flow velocity of the total gas flow towards the gas outlet 23 and through it out of the ion mobility spectrometer 100. Ions reaching the switching grid 11 are moved in a defined manner against the drift gas flow 13 in the direction of the ion detector 12 in the drift chamber by the potential support rings 31 arranged therein. The ion mobility of the ions can be determined on the basis of the measured drift times which the ions require for the distance from the switching grid 11 to the ion detector 12. It has been shown that the design of the ion mobility spectrometer 100 according to the present disclosure advantageously allows separation of ionised sample material and neutral particles formed by the ionisation source. Therefore, the ion mobility spectrometer 100 of the present disclosure can be used to determine an ion mobility spectrum that is largely free of interfering peaks, for example of NOx ions.

Figure 2:
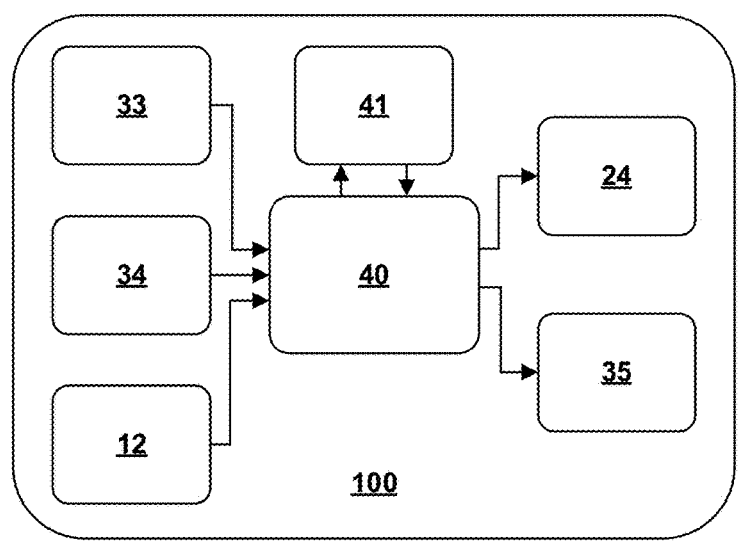
FIG. 2 is a schematic block diagram of an ion mobility spectrometer according to an embodiment.

FIG. 2 shows a schematic block diagram of an ion mobility spectrometer 100 according to the invention. In particular, this has a control unit 40 which is designed to carry out a method according to the invention for operating an ion mobility spectrometer 100 with minimum ignition voltage and is connected to the DBDI source 24 for this purpose. The control unit 40 is further connected to a pressure sensor 33 arranged in the reaction chamber 20 and to a temperature sensor 34 arranged in the reaction chamber 20. The control unit 40 is designed to receive from the pressure sensor 33 and the temperature sensor 34 a pressure value and a temperature value, respectively, detected near the DBDI source 24. The control unit is further designed to determine an optimum and, in particular, minimum ignition voltage for a DBDI source 24 on the basis of the received values and, if necessary, with access to a memory 41, and is further designed to control the DBDI source 24 for operation with this minimum ignition voltage. The control unit is further connected to an ion detector 12 arranged in the drift chamber 10 and is designed to receive at least one signal value from the ion detector 12, wherein a signal value corresponds to a quantity of a specific ion species detected with the ion detector 12 and/or to the integral or sum value in a drift time window of the drift time spectrum. The control unit 40 is further connected to a light source 35 and is further designed to control the light source 35 on the basis of the at least one signal value received from the ion detector 12. Also preferably, the control unit 40 is configured to control the DBDI source 24 on the basis of signal values received from the ion detector 12, in particular to set a minimum ignition voltage of the DBDI source 24 on the basis of the signal values.

Figure 3:
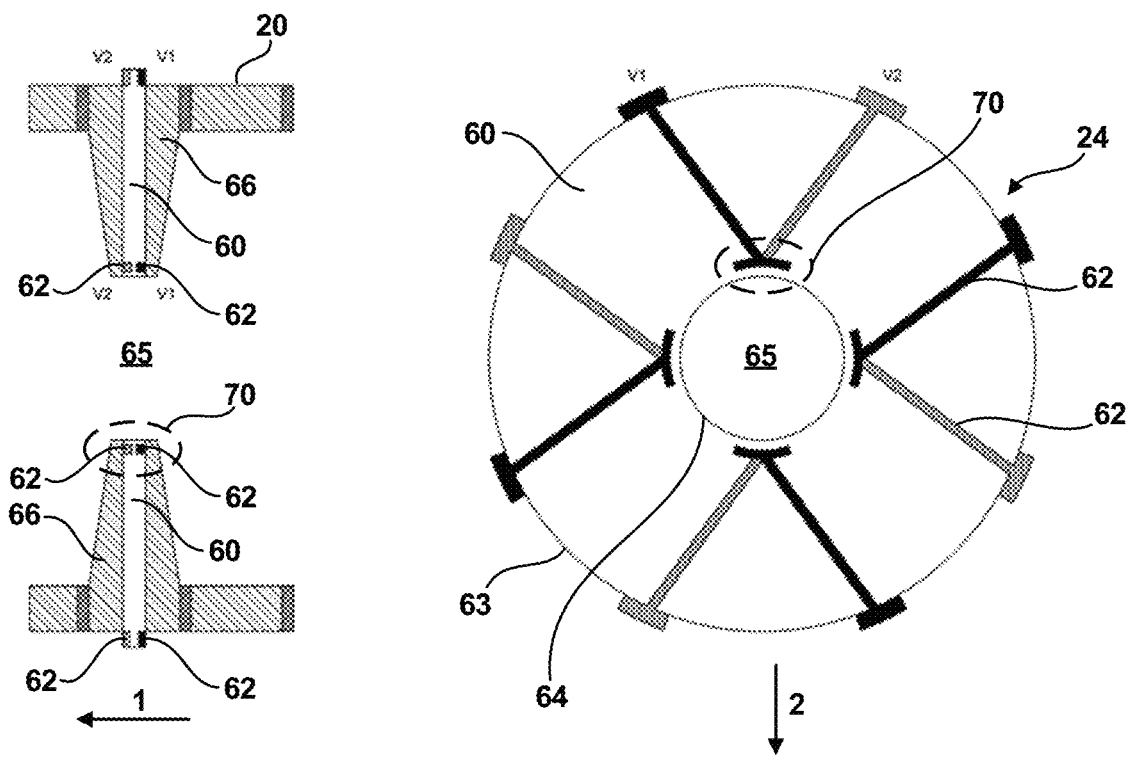
FIG. 3 is schematic views of a dielectric barrier discharge ionisation source, DBDI source, according to an embodiment in side and front view.

FIG. 3 shows a schematic view of a DBDI source 24 according to one embodiment in a side view (on the left) and in a frontal view (on the right). The DBDI source 24 is integrated here into the reaction chamber 20 of the ion mobility spectrometer 100 shown in FIG. 1 and has an insulating perforated disc 60 which is integrated in the axial direction between two segments of the reaction chamber 20. Upstream and downstream, the insulating perforated disc 60 is surrounded by flow conductors 66 which are intended to reduce the flow resistance of the perforated disc 60 for the drift flow and sample gas flow. The insulating perforated disc 60 has oppositely poled electrodes 62 on two surfaces pointing in different directions in the axial direction, in particular electrodes 62 with a first potential V1 on a first surface and electrodes 62 with a potential V2 on a second surface. The electrodes 62 extend from an outer circumference 63 of the insulating perforated disc 60 towards an inner circumference 64 of the insulating perforated disc 60 along the insulating perforated disc 60. At or near the outer circumference 63, the electrodes 62 are connected to electrical supply lines (not shown) which apply the relevant potential V1, V2 to the electrodes 62. The electrodes 62 extend in pairs in a V-shape and overlap with each other near the inner circumference 64, i.e., near a central opening 65 of the insulating perforated disc. In the frontal view, only the inner end of the electrodes of potential V1 is shown, but identical ends of the electrodes of potential V2 overlap on the opposite surface of the insulating perforated disc 60. A plasma zone 70 is thus formed between pairs of electrodes 62 of potentials V1, V2 when a suitable ignition voltage is applied. The plasma zone extends here along the inner circumference 64 in the central opening 65 of the insulating perforated disc 60. When the sample gas 22 or the mixture of sample gas 22 and drift gas in the drift gas flow 13 flows through the central opening 65, a low-temperature plasma is formed in the plasma zones 70, and thus primary ions are formed. As a result of subsequent reactions, product ions and possibly NOx ions are formed in the reaction chamber 20.

Figure 4:
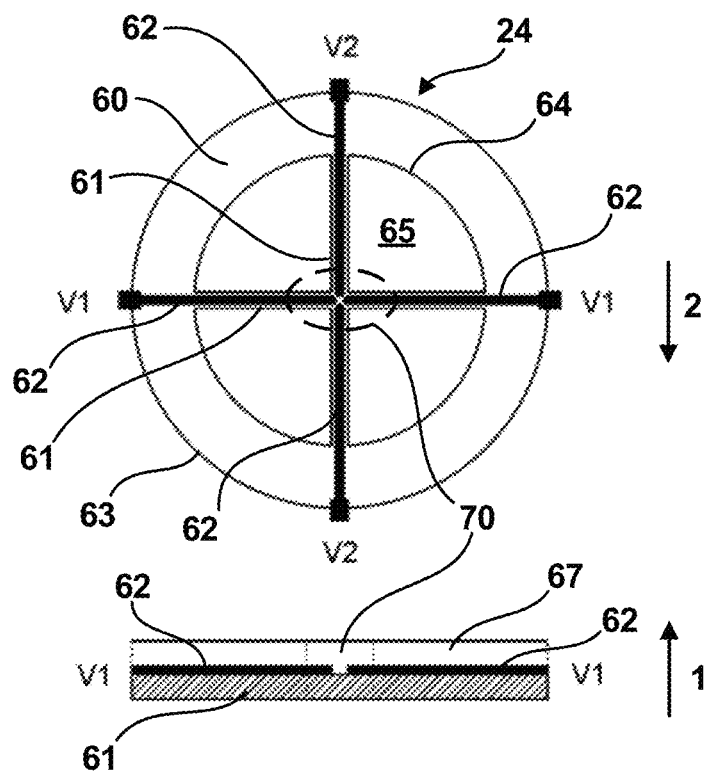
FIG. 4 is a schematic side and sectional view of a dielectric barrier discharge ionisation source, DBDI source, according to a further embodiment.

FIG. 4 shows a schematic side and sectional view of a DBDI source 24 according to a further embodiment. The same reference signs are used for the same elements in FIG. 4 as in FIG. 3, and an explanation of the DBDI source 24 of FIG. 4 is given in particular insofar as this DBDI source 24 differs from that of FIG. 3. The DBDI source 24 also has the insulating perforated disc 60 and insulating spokes 61 monolithically formed therewith, which extend over the central opening 65 and cross in the centre of the DBDI source 24 in the central opening 65. In particular, the DBDI source 24 has two spokes 61 oriented at right angles to each other. Two electrodes 62 are arranged on each spoke and extend from the outer circumference 63 towards the inner circumference 64 and beyond. The electrodes 62 extend to just before the centre of the DBDI source 24, which is preferably located on the axis of rotational symmetry of the reaction chamber 20. The electrodes 62 formed on a spoke 61 are each at a first electrical potential V1 or a second electrical potential V2. Therefore, in the centre of the DBDI source 24, two electrodes 62 are arranged at right angles to each other in each case and are located at different electrical potentials V1, V2. Therefore, an ignition voltage $\Delta V = V1 - V2$ is applied between each of these electrodes 62 and a total of four plasma zones 70 are formed between the electrodes 62 arranged at right angles to each other. The DBDI source 24 of FIG. 4 is arranged in the reaction chamber 20 in the same way as the DBDI source 24 of FIG. 3, wherein the electrodes 62 are arranged on spokes 61 on the gas outlet side. Therefore, an optimal flow around the plasma zones 70 is ensured, and at the same time electrically neutral nitrogen oxide compounds are transported optimally to the gas outlet 23.

Figure 5:
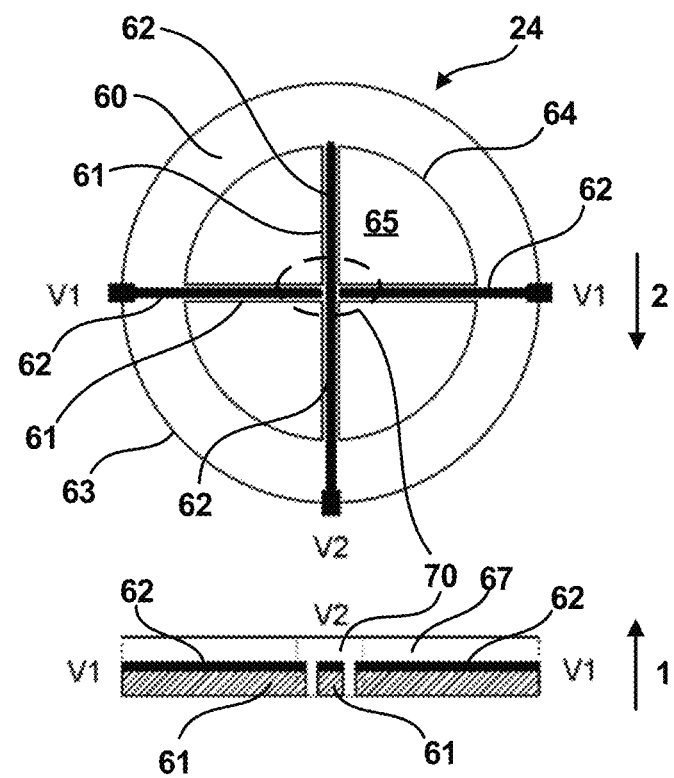
FIG. 5 is a schematic side and sectional view of a dielectric barrier discharge ionisation source, DBDI source, according to a further embodiment.

FIG. 5 shows a schematic side and sectional view of a DBDI source 24 according to a further embodiment. The same reference signs are used for the same elements in FIG. 5 as in FIG. 4, and an explanation of the DBDI source 24 of FIG. 5 is given in particular insofar as this DBDI source 24 differs from that of FIG. 4. The DBDI source 24 of FIG. 5 has the same insulating perforated disc 60 and the same insulating spokes 61 as the DBDI source 24 of FIG. 4, but the electrodes 62 are designed differently. In particular, one electrode 62 at the potential V2 extends continuously over the central opening 65, i.e., over an entire spoke 61. On the spoke 61 arranged at right angles thereto, there are arranged two electrodes 62 at the potential V1, each extending from the insulating perforated disc 60 to the centre of the DBDI source 24. Therefore, two plasma zones 70 are formed between the ends of the electrodes 62 at potential V1 and the electrode 62 at potential V2.

Figure 6:
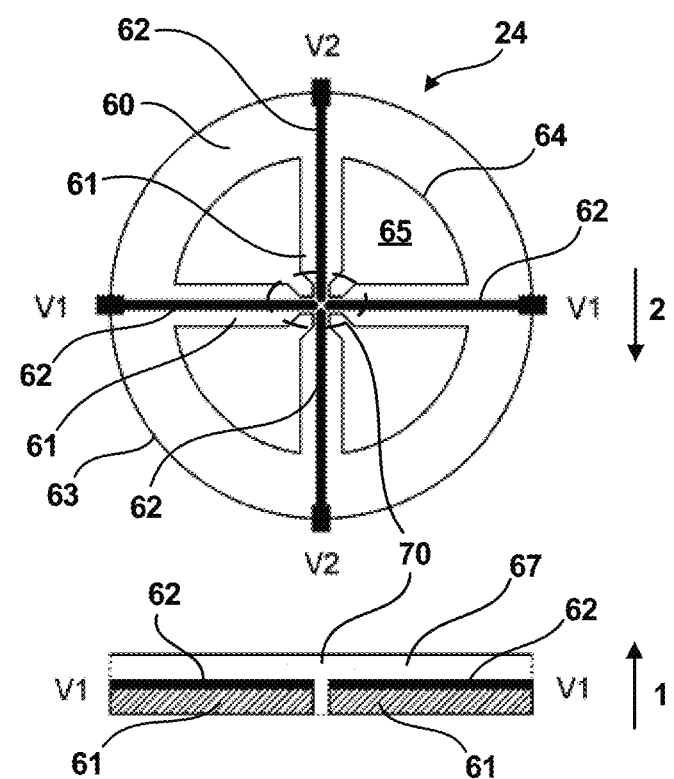
FIG. 6 is a schematic side and sectional view of a dielectric barrier discharge ionisation source, DBDI source, according to a further embodiment.

FIG. 6 shows a schematic side and sectional view of a DBDI source 24 according to a further embodiment. The same reference signs are used for the same elements in FIG. 6 as in FIG. 4, and an explanation of the DBDI source 24 of FIG. 6 is given in particular insofar as this DBDI source 24 differs from that of FIG. 4. The electrode arrangement of the DBDI source 24 of FIG. 6 corresponds to the electrode arrangement of the DBDI source 24 of FIG. 4; only the insulating spokes 61 are different. In particular, the insulating spokes 61 are wider near the insulating perforated disc 60 than in FIG. 4, but taper near the centre of the DBDI source 24. This advantageously achieves better stability of the DBDI source 24, and yet small air gaps for forming the plasma zones 70.

Figure 7:
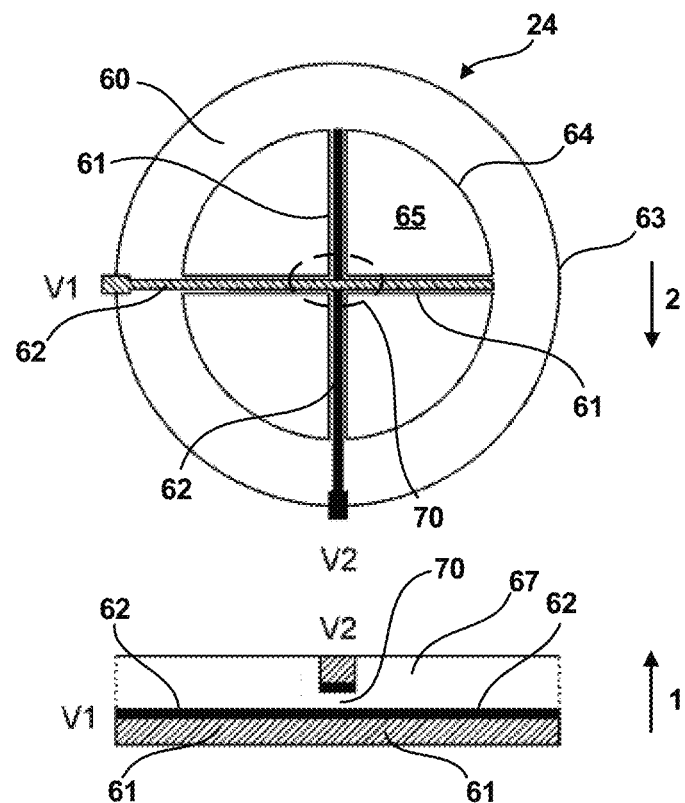
FIG. 7 is a schematic side and sectional view of a dielectric barrier discharge ionisation source, DBDI source, according to a further embodiment.

FIG. 7 shows a schematic side and sectional view of a DBDI source 24 according to a further embodiment. The same reference signs are used for the same elements in FIG. 7 as in FIG. 5, and an explanation of the DBDI source 24 of FIG. 7 is given in particular insofar as this DBDI source 24 differs from that of FIG. 5. The DBDI source 24 of FIG. 7 has two spokes 61, each of which extends over the entire central opening 65 and is offset from one another in the axial direction. On each of the spokes 61, an electrode 62 extends across the entire width of the central opening, with the two electrodes 62 being connected to one each of the potentials V1, V2.

Figure 8:
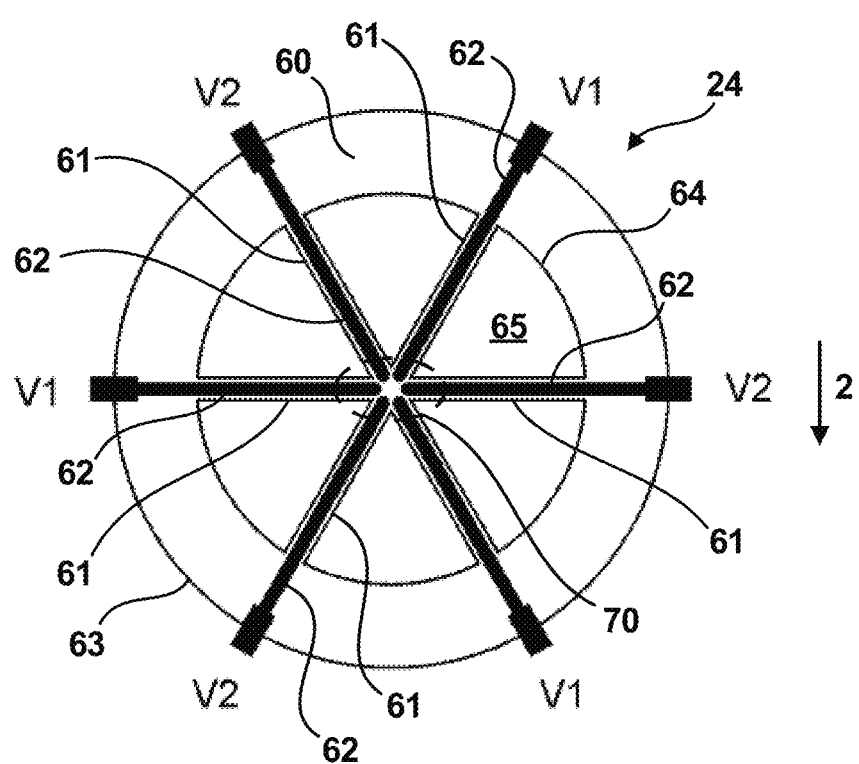
FIG. 8 is a schematic side view of a dielectric barrier discharge ionisation source, DBDI source, according to a further embodiment.

FIG. 8 shows a schematic side and sectional view of a DBDI source 24 according to a further embodiment. The same reference signs are used for the same elements in FIG. 8 as in FIG. 5, and an explanation of the DBDI source 24 of FIG. 8 is given in particular insofar as this DBDI source 24 differs from that of FIG. 5. The DBDI source 24 of FIG. 8 has in particular three spokes 61 which are formed monolithically with the insulating perforated disc 60 and have the same sector angles to each other. In particular, two spokes 61 adjacent to each other in the circumferential direction each enclose angles of 60° with each other. Two electrodes 62 are arranged on each of the spokes 61, one of which has the potential V1 applied to it and the other of which has the potential V2 applied to it. Therefore, a total of three electrodes 62 are at the electric potential V1 and three electrodes 62 are at the electric potential V2, so that when a minimum ignition voltage is applied, a total of six plasma zones 70 are formed between the tips of circumferentially adjacent electrodes 62.

Figure 9A:
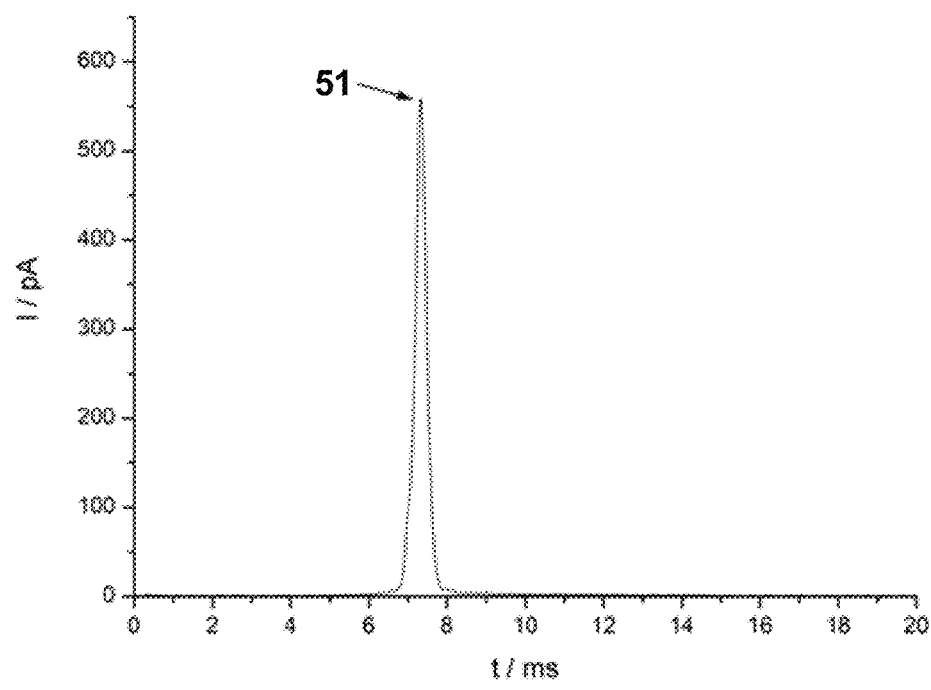
FIGS. 9(A) and 9(B) are IMS spectrums of negatively charged ions (see FIG. 9(A)) without and (see FIG. 9(B)) with the presence of contaminating NOx ions in the drift chamber.
Figure 9B:
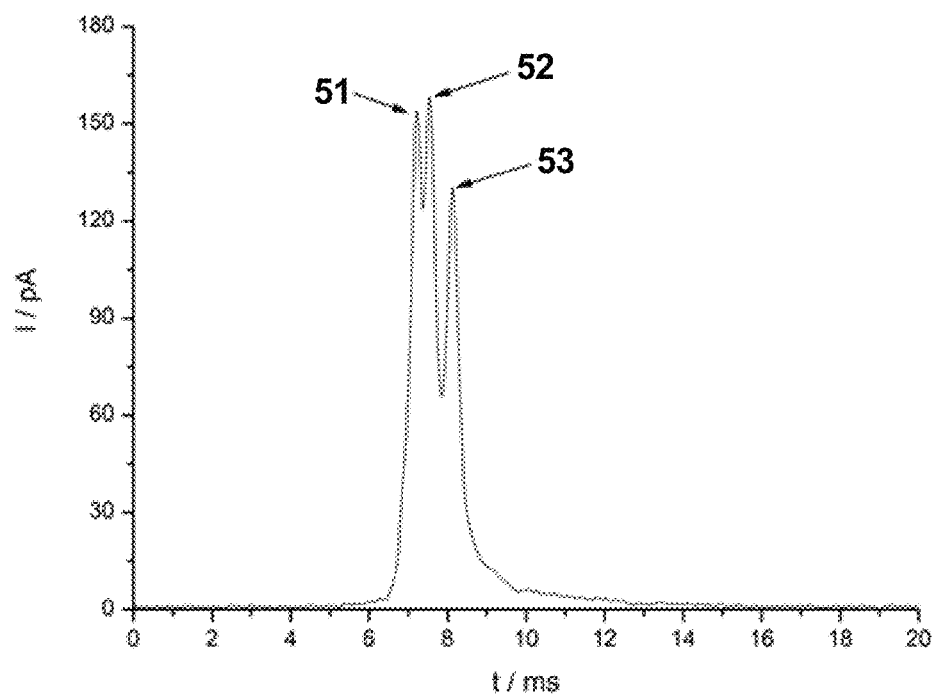

FIGS. 9(A) and (B) show drift time spectra determined with the ion mobility spectrometer 100 according to the invention without (FIG. 9(A)) and with (FIG. 9(B)) contamination of the sample gas with NOx ions. FIG. 9(B) shows a drift time spectrum that was generated at an ignition voltage of the DBDI source 24 above an optimum ignition voltage. The excessively high ignition voltage causes NOx ions to be formed at the DBDI source 24, for example $NO_2$ ions and/or $NO_3$ ions. FIG. 9(B) shows two characteristic peaks 52, 53 for NOx ions in the ion mobility spectrum. The second IMS peak 52 corresponds to a value of a normalised ion mobility $K_0^{52}$ of 2.18 cm$^2$/Vs and the third IMS peak 53 to a value of a normalised ion mobility $K_0^{53}$ of 2.00 cm$^2$/Vs.

Also shown is a first IMS peak 51 of an exemplary ionised sample material with an ion mobility $K_0^{51}$ of 2.126 cm$^2$/Vs. As can be seen from FIG. 9(B), a resolution of the first IMS peak 51 is clearly hindered by the IMS peaks 52, 53 of the NOx ions. Therefore, a measurement of the IMS peak 51 should be carried out without the presence of NOx ions if possible. Therefore, it is advantageous that in the ion mobility spectrometer 100 according to the invention the minimum ignition voltage is determined and set by the control unit 40 on the basis of the measured pressure and temperature values near the DBDI source 24. In this way, the formation of NOx ions can be avoided and consequently the drift time spectrum of FIG. 9(A) is determined exclusively with the IMS peak 51.

REFERENCE SIGNS

1 axial direction
2 radial direction
10 drift chamber
11 switching grid
12 ion detector
13 drift gas flow
14 drift gas inlet
20 reaction chamber
21 sample gas inlet
22 sample gas
23 gas outlet
24 dielectric barrier discharge ionisation source, DBDI source
25 gas inlets
30 potential source
31 field support ring
32 reference potential
33 pressure sensor
34 temperature sensor
35 radiation source (LED, laser)
40 control unit
41 memory
51 first IMS peak
52 second IMS peak
53 third IMS Peak
60 insulating perforated disc
61 insulating spoke
62 electrode
63 outer circumference
64 inner circumference
65 central opening
66 flow conductor
67 insulating seal
70 plasma zone
100 ion mobility spectrometer
V1 first potential
V2 second potential

The invention claimed is:

1. An ion mobility spectrometer for determining the ion mobility of a sample gas in dry air as drift gas and comprising a drift chamber and a reaction chamber, the ion mobility spectrometer comprising:
   a dielectric barrier discharge ionisation source, DBDI source, arranged in the reaction chamber for ionising the sample gas;
   a pressure sensor arranged in the reaction chamber and a temperature sensor arranged in the reaction chamber;
   a light source for irradiating the DBDI source with light in a wavelength range from 240 nm to 480 nm; and
   a control unit, which is connected to the pressure sensor, the temperature sensor, the DBDI source and the light source and which is configured to set an ignition voltage of the DBDI source and further configured to control the light source depending on a pressure value determined by the pressure sensor and a temperature value determined by the temperature sensor.

2. The ion mobility spectrometer according to claim 1, further comprising an ion detector arranged in the drift chamber, wherein the control unit is also configured to receive a signal value from the ion detector and to control the DBDI source and/or the light source on the basis of the signal value.

3. The ion mobility spectrometer according to claim 2, wherein the control unit is also configured to control the light source such that a first signal value of the ion detector exceeds a first limit value.

4. The ion mobility spectrometer according to claim 1, wherein the control unit is further configured to set an ignition voltage of the DBDI source in such a way that, for the determined pressure and temperature values, a first signal value of an ion detector exceeds a first limit value and a second signal value of the ion detector falls below a second limit value.

5. The ion mobility spectrometer according to claim 2, wherein the control unit is further configured to determine the first signal value on the basis of a peak of a product ion and the second signal value on the basis of a peak of a NOx ion in an ion mobility spectrum determined with the ion detector.

6. The ion mobility spectrometer according to claim 1, wherein the light source is configured to irradiate the DBDI source with light of a wavelength of 365 nm, 385 nm, 395 nm, 405 nm, 405 nm or 450 nm and/or with light of an optical power of less than 100 mW.

7. The ion mobility spectrometer according to claim 1, wherein the reaction chamber is cylindrical, and wherein the DBDI source has an insulating perforated disc, the outer circumference of which is integrated into an edge of the reaction chamber, and wherein at least two oppositely poled electrodes extend from the outer circumference of the insulating perforated disc towards an inner circumference of the insulating perforated disc, and wherein at least one plasma zone is formed between the oppositely poled electrodes.

8. The ion mobility spectrometer according to claim 7, wherein the DBDI source has at least two insulating spokes, which each extend over a central opening of the insulating perforated disc, cross each other within the central opening and support at least one of the electrodes.

9. The ion mobility spectrometer according to claim 8, wherein the insulating perforated disc and the insulating spokes are monolithic and/or are formed from an electrically insulating glass, plastic, quartz or ceramic.

10. The ion mobility spectrometer according to claim 8, wherein the reaction chamber and the perforated disc are formed concentrically in a circular-cylinder shape, the insulating spokes are oriented radially and cross each other on an axis of symmetry of the reaction chamber and perforated disc, and the at least one plasma zone is formed at the crossing point of the insulating spokes.

11. The ion mobility spectrometer according to claim 8, wherein the reaction chamber has a gas outlet, the DBDI source is arranged at the gas outlet, and the electrodes are arranged on a side of the DBDI source facing the gas outlet.

12. The ion mobility spectrometer according to claim 8, wherein each of the insulating spokes has a trench and one of the electrodes is located in the trench, and/or wherein the electrodes are coated with an insulating seal.

13. The ion mobility spectrometer according to claim 12, wherein the insulating seal is formed from UV-transparent material and is configured as a light guide for the light of the light source with an exit point near the at least one plasma zone.

14. A method of a control unit for operating an ion mobility spectrometer, having a drift chamber and a reaction chamber, for determining the ion mobility of a sample gas in dry air as drift gas, the method comprising:
   determining a pressure value detected by a pressure sensor arranged in the reaction chamber and a temperature value detected by a temperature sensor arranged in the reaction chamber;
   setting an ignition voltage of a DBDI source arranged in the reaction chamber depending on the determined pressure value and the determined temperature value; and
   controlling a light source arranged in the reaction chamber for irradiating the DBDI source with light in a wavelength range from 240 nm to 480 nm.

15. The method according to claim 14, further comprising at least one of:
   receiving a signal value from an ion detector arranged in the drift chamber;
   setting the ignition voltage depending on the pressure and temperature values, so that a first signal value of the ion detector exceeds a first limit value and a second signal value of the ion detector falls below a second limit value; and
   controlling the light source so that the first signal value of the ion detector exceeds a first limit value.

* * * * *